United States Patent [19]

Jensen et al.

[11] Patent Number: 4,917,867
[45] Date of Patent: Apr. 17, 1990

[54] APPARATUS FOR THE COLLECTION AND TRANSPORTATION OF DUAL BIOLOGICAL SAMPLES

[75] Inventors: Richard E. Jensen, St. Peter; Donald H. Nichols, Roseville; D. Gary Hemphill, Wayzata, all of Minn.

[73] Assignee: Forensic Applications Corporation, Minneapolis, Minn.

[21] Appl. No.: 212,016

[22] Filed: Jun. 27, 1988

Related U.S. Application Data

[63] Continuation-in-part of Ser. No. 89,586, Aug. 26, 1987, Pat. No. 4,873,193.

[51] Int. Cl.$^4$ ............................................. B01L 3/00
[52] U.S. Cl. ..................................... 422/102; 422/61
[58] Field of Search ..................... 220/23, 83, 406; 206/499, 514–517, 828; 215/10, DIG. 3; 422/61, 102; 436/176

[56] References Cited

U.S. PATENT DOCUMENTS

| | | | |
|---|---|---|---|
| 3,849,256 | 11/1974 | Linder | 422/102 |
| 3,883,745 | 5/1975 | Glasser | 422/102 |
| 4,094,641 | 6/1978 | Friswell | 422/102 |
| 4,418,702 | 12/1983 | Brown et al. | 422/102 |

Primary Examiner—Barry S. Richman
Assistant Examiner—T. J. Wallen
Attorney, Agent, or Firm—Moore & Hansen

[57] ABSTRACT

An apparatus for collecting and transporting dual biological samples such as blood and urine comprising an impact resistant outer container having a soft foam cushioning pad disposed across the bottom, and a thicker protective collar of dense foam placed on top of the cushioning pad. The protective collar defines bores extending therethrough and sized to receive a tamper resistant sealed specimen vial and lid assembly, a pair of blood sampling tubes, and a multi-sample sterile syringe assembly. An instruction manual, tamper evidencing sealing tapes, and a non-alcoholic swab are enclosed in the outer container, along with an upper cushioning pad similar to that at the bottom of the container. The outer container is then closed with a lid and sealed in a temper evidencing wrapper.

15 Claims, 2 Drawing Sheets

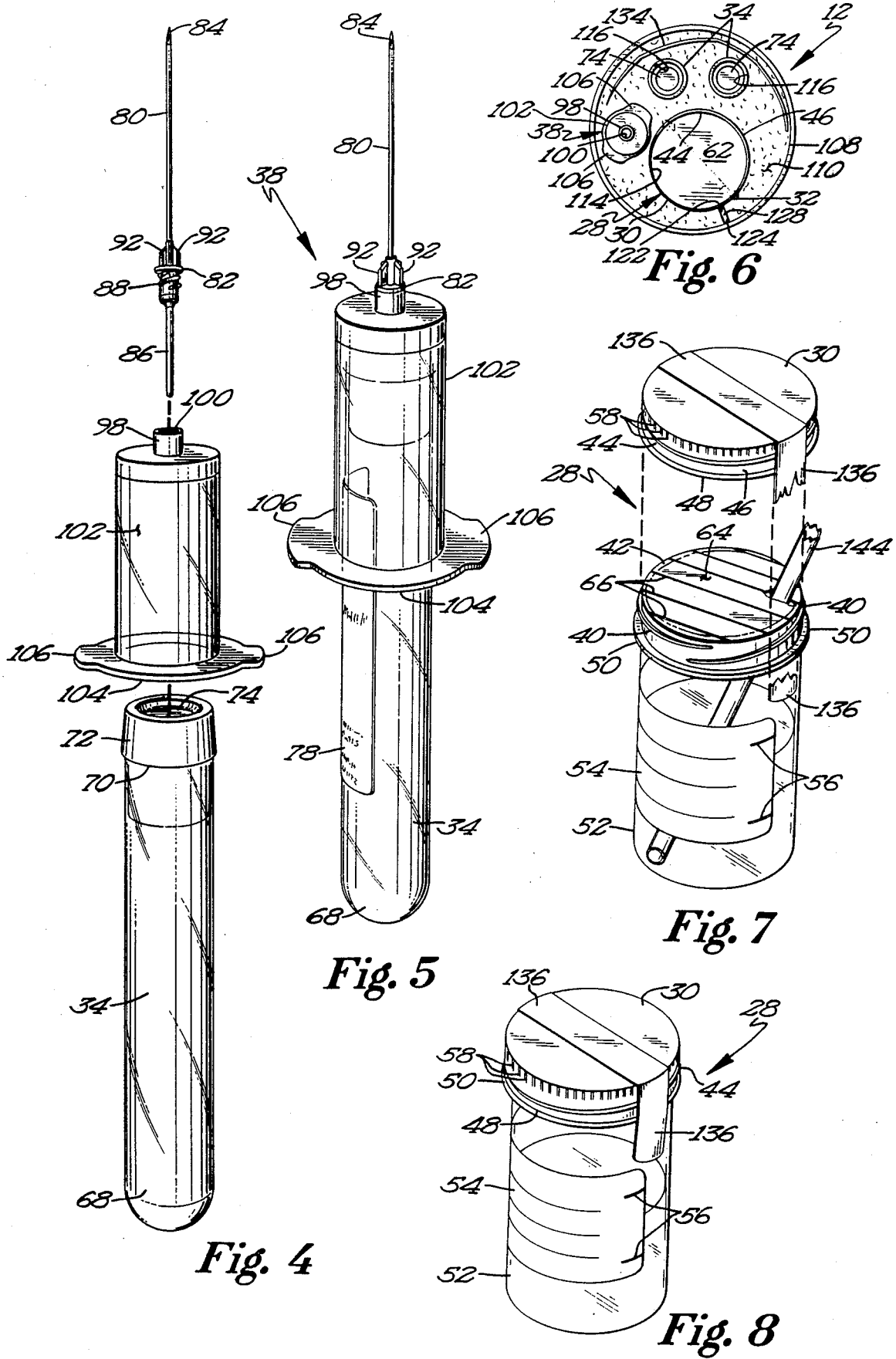

# APPARATUS FOR THE COLLECTION AND TRANSPORTATION OF DUAL BIOLOGICAL SAMPLES

This is a continuation-in-part of the pending application Ser. No. 07/089,586 filed on Aug. 26, 1987, U.S.P. 4,873,193.

BACKGROUND OF THE INVENTION

The present invention relates generally to devices for collecting and transporting biological samples, and particularly to a method and apparatus for preserving collecting and transporting evidentiary samples for analytical testing.

Some of the practical and evidentiary concerns associated with the design of devices for collecting and transporting biological samples are outlined in U.S. Pat. No. 4,873,193 which relates to a method and apparatus for the collection and transportation of biological specimens such as urine and similar biological substances.

Besides the evidentiary considerations for keeping the containers sealed and secure prior to use, there is the concern that the equipment used for blood sampling must be kept sterile to prevent contamination or the transfer of communicable diseases.

Conventionally, small blood samples for white blood cell counts were taken by pricking a finger of the patient and removing an aliquot of blood by pipette or capillary tube, and placing that sample on a microscope slide for inspection. More complicated testing requires taking a larger sample, which was traditionally performed using a pipetting catheter. The donation of large blood samples on the order of one pint for use in transfusions or blood component separation is normally accomplished using a larger vein puncturing cannula and sterile catheter and bag assembly familiar to the art. More recently, complex machines which separate blood components and extract only certain elements, such as platelets or leukocytes, and which return the remainder of the fluid blood components to the patient have been developed. These machines generally operate on the principal of centrifugal elutriation or one of various filtration methods, such as shown in U.S. Pat. No. 4,680,025.

Sampling blood for evidentiary purposes present some particular problems not addressed by these conventional devices. Several are useful only for microsamples, and two individual samples of moderate size are generally required for evidentiary purposes, one for presumptive testing and a spare for alternate or backup use. The more complicated machines or larger catheters can be used to take moderate sized samples, but are either very expensive, not mobile, or do not provide for the storage and transportation of individual samples in a manner suitable for analytical testing or evidentiary use. Moreover, none of the existing devices satisfy the legal and evidentiary requirements for maintaining a valid chain of custody from prior to sampling until testing.

Specialized devices for taking blood samples for testing are known to the art, representative examples being disclosed in U.S. Pat. Nos. 4,385,637 on a syringe-like blood sampler; 3,366,103 on a blood collecting assembly; 4,494,882 on a method and device for collecting, transporting, and delivering micro-samples of blood; 4,409,990 on a fluid sampling needle assembly and method of use thereof; 4,320,769 on a universal holder or blood collecting tubes; and 3,901,219 on a blood collecting container and method.

Of these types of devices, the most commonly utilized blood sampler is the assembly comprising a multi-sample needle, an evacuated blood sampling tube, and a holder for combining the two in an operable configuration. One such assembly is marketed under the name Vacutainer by the Becton, Dickinson and Company of New Jersey. Many patents disclosing improvements and modifications in such a device are known, representative examples of this type of a device being shown in U.S. Pat. Nos. 4,317,456 and 4,436,098. The improvements and modifications generally relate to vein entry indicators, anti-backflow valves, stopper configurations, and the like.

These devices generally do not address the problem of storing and transporting the contents of the sample vial, or of the device or assembly prior to sampling. Composite samples of distinct biological substances such as blood and urine raise distinct problems. Specimens such as urine are usually contained in larger receptacles, and care must be taken to prevent their breakage and to keep them from damaging the blood samples. The components conventionally used for blood sampling generally include such items as fragile glass vacuum tubes and syringe needles, which require greater care in handling and during transportation. As with any medical "sharp," care must also be taken to permit easy access to and use of the equipment, in order to prevent accidental injury to the medical personnel. A system for storing or transporting distinct samples must allow the person taking and handling the samples to keep track of and conveniently work with the samples and the sampling equipment, and to safely store and protect those components not being used.

BRIEF SUMMARY OF THE INVENTION

It is therefore one object of this invention to design an apparatus for easily and efficiently collecting and transporting composite samples of more than one fluid biological evidence such as blood and urine.

It is a further object of this invention to design the above apparatus such that the chain of custody for the evidentiary samples to be contained therein may be properly and effectively maintained so as to prevent tampering with the samples or with the apparatus prior to taking the samples.

It is a further object of this invention to design the above apparatus such that a specimen vial and fragile glass sample tubes filled with samples of blood and urine may be transported without risk of damage or loss of integrity due to rough handling, droppage, or the like.

It is still another object of this invention to design the above apparatus such that it may also function as a utility rack for the additional sampling equipment while one of the evidentiary samples is being taken.

Briefly described, the apparatus for collecting and transporting dual biological samples of this invention comprises an impact resistant outer container having a soft foam cushioning pad disposed across the bottom, and a thicker protective collar of dense foam placed on top of the cushioning pad. The protective collar defines apertures or bores extending therethrough to receive a tamper resistant sealed specimen vial and lid assembly, a pair of blood sampling tubes, and a multi-sample sterile syringe assembly. An instruction manual, tamper evidencing sealing tapes, and a non-alcoholic swab are enclosed in the outer container, along with an upper cushioning pad similar to that at the bottom of the container. The outer container is then closed with a lid and sealed in a similar tamper evidencing wrapper.

The apparatus for collecting and transporting dual biological samples of this invention may be subjected to extraordinarily rough handling, such as being thrown against a wall or similar abuse, with the contents of the blood sampling tubes and specimen vial remaining intact.

BRIEF DESCRIPTION OF THE DRAWINGS

FIG. 4 is an exploded perspective view of the blood sampling tube, holder, and syringe assembly of the apparatus of FIG. 1;

FIG. 5 is a perspective view of the blood sampling tube, holder, and syringe assembly of the apparatus of FIG. 4 in the assembled configuration for sampling;

FIG. 6 is a top view of the contents of the container taken through the line 6—6 of FIG. 1;

FIG. 7 is a perspective view of the specimen vial of the apparatus of FIG. 1 with the lid removed and a pipette removing an aliquot of the sample; and FIG. 8 is a perspective view of the specimen vial of the apparatus of FIG. 1 with the lid and sealing tapes secured.

DESCRIPTION OF THE PREFERRED EMBODIMENT

The apparatus for collecting and preserving sample of distinct fluid biological evidence of this invention is shown in FIGS. 1-8 and referenced generally therein by the numeral 10.

Figure 1:
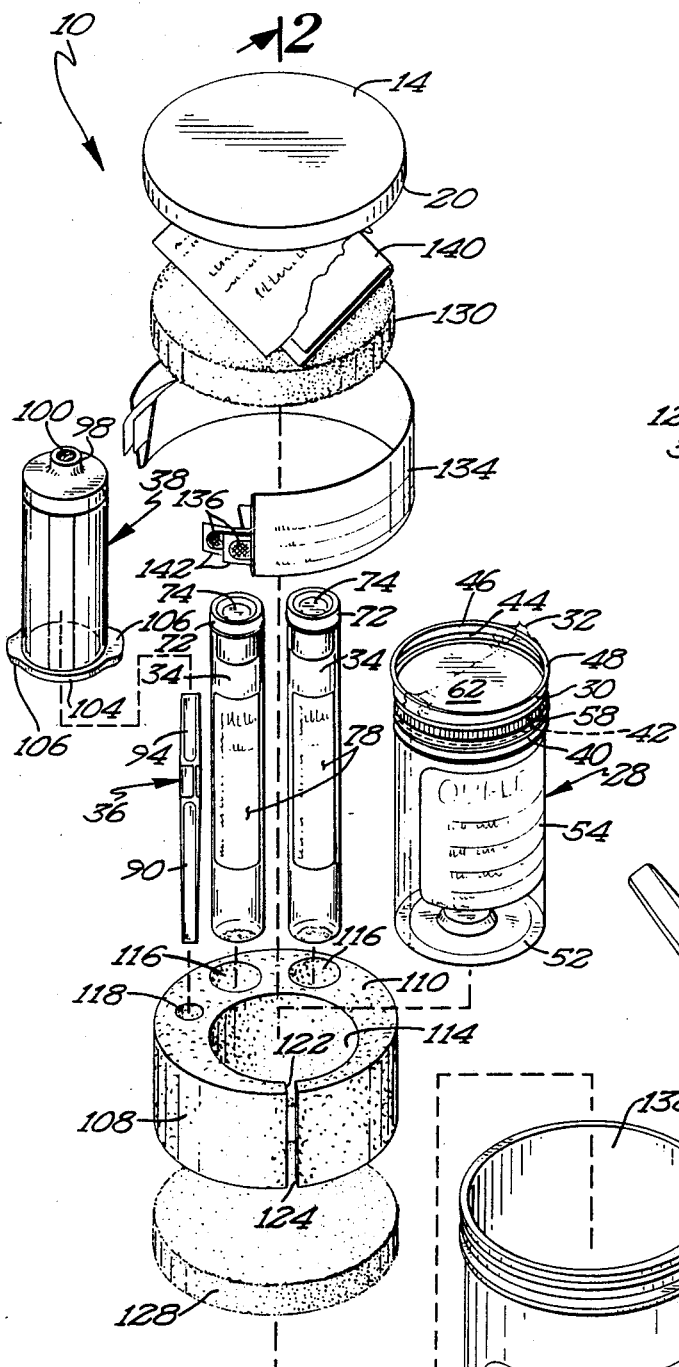
FIG. 1 is an exploded perspective view of the apparatus for collecting and transporting dual biological samples of this invention.

Referring to FIG. 1, it may be seen that the apparatus 10 is contained within an outer container having a generally cylindrical, plastic outer container body 12 defining a receptacle region therein, and with a removable lid 14 having inner threads (not shown) aligned to engagingly mesh or seal with threads 16 along or below the rim 18 of the container body 12. The lower edge 20 of the lid 14 also abuts against the upper surface of a sealing collar 22 which projects approximately perpendicularly from the outer wall surface 24 of the outer container body 12. An adhesive mailing or routing label 26 is attached to the outer wall surface 24 of the outer container body 12 having pertinent information such as the mailing address of an analytical testing laboratory or other predetermined destination preprinted thereon, or having the necessary space available for such information to be added. The outer container 12 and lid 14 should be molded from a resilient, highly impact resistant, opaque plastic resin, and is initially wrapped with a tamper resistant and tamper evident transparent shrink-wrap (not shown).

Figure 2:
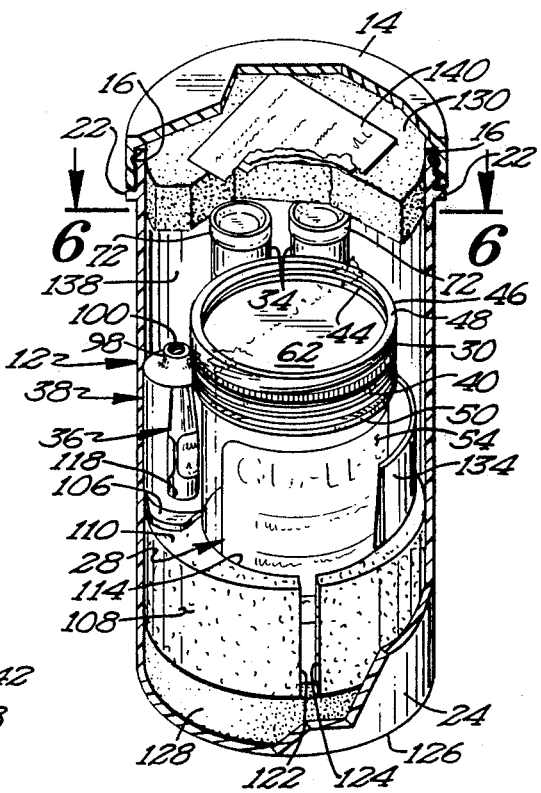
FIG. 2 is a partially cut away perspective view of the apparatus of FIG. 1 showing the contents in the initial configuration.

Referring to FIGS. 1 and 2, it may be seen that slidably received within the outer container 12 are an inner specimen vial 28 and associated vial lid 30 sealed in a protective wrapper 32, a pair of blood sampling tubes 34, a blood sampling syringe assembly 36, and a holder and protective guard 38 for the blood sampling tubes 34 and syringe 36.

The inner container or specimen vial body 28 is manufactured from a uniform mixture of polystyrene and K-resin, having a generally cylindrical shape and a capacity of approximately 90-100 cc., as described in the above referenced co-pending parent application. The specimen vial 28 should be substantially transparent or translucent, or should have a clear window portion extending the height of the specimen vial 28, such that the level or quantity of any fluid content within the receptacle region of the vial body 28 can be readily and visibly observed. Referring to FIGS. 7 and 8, it may be seen that the open top portion of the specimen vial 28 has a threaded region 40 adjacent the top rim 42 which are sized and aligned to sealing engage threads 44 along the inside of the skirt portion 46 of the lid 30. The lower edge 48 of the skirt 46 of the lid 30 is similarly designed to sealingly contact a sealing collar 50 projecting from the body surface 52 of the specimen vial 28 below the threaded region 40.

An adhesive backed specimen identification label 54 is attached to the outer body surface 52 of the specimen vial 28, the specimen identifying label 54 having the appropriate preprinted information identifying the source of the specimen vial 28, and suitable space available for identifying the individual or entity supplying the fluid evidence contained therein. The specimen vial should also contain a pair of indicators 56 which specify the minimum and maximum specimen quantity which is necessary for testing, and which ensures the safe transportation of the specimen vial 28. In the case of a transparent or translucent specimen vial 28, the indicators 56 may comprise preprinted lines on the specimen label 54 positioned and aligned to correspond to the minimum and maximum levels associated with the particular dimensions of the container. In the case of human urine specimens, the upper and lower limit indicators 56 should designate approximately 65 cc. and 25 cc. respectively.

The lid 30 for the specimen vial 28 has a knurled or serrated peripheral edge 58 which aids in securing the lid 30 onto the threaded portion 40 of the vial 28 to form an engaging and fluid-tight seal. A styrene foam sealing disk 60 is inserted into the lid 30 for the specimen vial 28, the disk 60 having an adhesive coated surface 62, and a non-adhesive coated, opposite surface 64 having generally linear printed lines or text 66 extending across it.

Initially, the specimen vial 28, lid 30, and foam sealing disk 60 are sealed together within a generally brittle, tamper resistant wrapper 32 made from a clear plastic thermal shrink-wrap material. The lid 30 is initially inverted on the vial 28, with the foam sealing disk 60 inserted within the lid 30 such that the lower edge 48 of the lid 30 and adhesive surface 62 of the sealing disk 60 are facing upwards, away from the specimen vial 28.

A 1000 mg. portion of granular sodium fluoride, or other suitable chemical agent which will not interfere with the analytical testing, may initially be placed within the specimen vial 28 and will preserve the fluid sample until such time that the specimen vial 28 is unsealed and opened for analysis.

Referring to FIGS. 1 and 2, it may be seen that slidably received within the outer container 12 are the inner specimen container 28 and associated lid 30 sealed in a protective wrapper 32, the pair of blood sampling tubes 34, the blood sampling syringe assembly 36, and the holder and protective guard 38 for the blood sampling tubes 34 and syringe 36.

Figure 3:
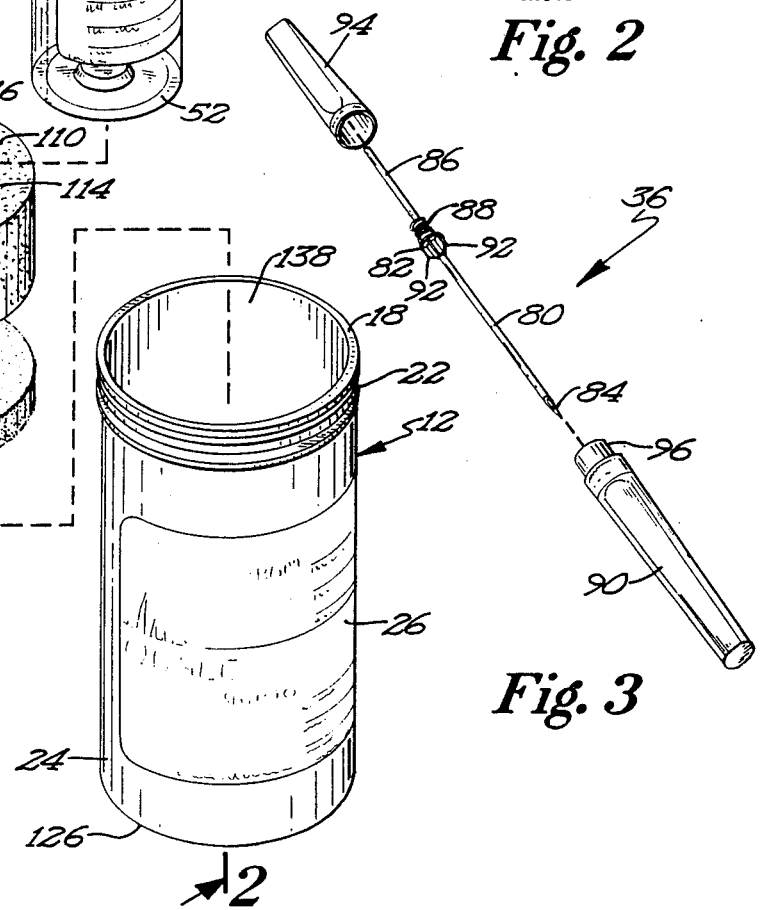
FIG. 3 is an exploded perspective view of the multisample syringe assembly of the apparatus of FIG. 1.

Referring particularly to FIGS. 3-5, it may be seen that the blood sampling tubes 34, blood sampling syringe assembly 36 and holder and protective guard 38 may be of a type known to the art and described in detail in the above referenced patents. The Becton, Dickinson & Co. Vacutainer brand blood sampling units have proven suitable for this application.

Each blood sampling tube 34 comprises a glass, sterile interior, round-bottomed test tube 68 having an open top and being sealed or closed at the circular rim 70 thereof by a stopper 72 having a thin membrane covering 74 and a thicker cylindrical side wall portion 76 which depends into the top of the tube 34 and forms a sealing closure therewith. Each tube 34 may be manufactured so as to produce a gentle vacuum therein, and may include a small aliquot of a dry preservative compound such as a less than one gram mixture of potassium oxalate and sodium fluoride. An adhesive backed specimen identification label 78 is similarly attached to the outer surface 52 of each tube 34 the label 78 having the appropriate preprinted information identifying the source of the tube 34, and suitable space for identifying the individual or entity supplying the blood sample contained therein.

The sterile, multi-sample blood sampling syringe assembly 36 consists of a long syringe needle 80 or double ended cannula defining a longitudinal bore and being mounted to and passing entirely through an intermediate retaining collar 82. The needle or cannula 80 has a pair of opposing sharpened, bias cut ends 84, with one end 84 of the needle 80 projecting from the collar 82 a distance greater than the opposing end 84. The shorter, opposing end is covered by a thin rubber protective sheath 86 which is attached to the collar 82 such that no portion of that end 84 of the needle 80 is exposed. The collar 82 is molded from an impact resistant plastic and includes a plurality of threads 88 on the side facing the shorter end 84 of the needle 80. The long end 84 of the needle 80 is covered by a first protective cap 90 which snaps over of frictionally engages a plurality of tines 92 on the side of the collar 82 opposing the threads 88, with the short end 84 of the needle 80 being covered by a second protective cap 94 which snaps over and frictionally engages a recessed region 96 of the first protective cap 90 to enclose the syringe needle 80.

As shown in FIGS. 4 and 5, the holder and protective guard 38 is molded from an impact resistant plastic and includes a narrow neck region 98 defining a bore 100 having internal threads corresponding to the threads 88 on the collar 82 of the blood sampling syringe assembly 36, a generally cylindrical body 102 defining an interior region of sufficient size to accommodate the top of the sample tubes 34 including the stoppers 72, and an outwardly extending radial gripping collar 104 having opposing side extensions 106.

The second protective cap 94 may be removed from the shorter end 84 of the syringe needle 80 while gripping the first protective cap 90 and the threaded portion 88 of the collar 82 inserted into the bore 100 of the holder and protective guard 38 and rotated to engage the threads 88 of the collar 82 and securely mount the syringe needle 80 to the holder and protective guard 38. The holder and protective guard 38 is then placed over the top of one of the tubes 34 and pressed downward thereon, causing the shorter end 84 of the needle 80 to pierce the protective cover 86 and the thin membrane 74 in the stopper 72, and enter the interior region of the tube 34. The fingers of a persons hand may grip the outwardly extending radial gripping collar 104 and opposing side extensions 106 to exert a continuous pressure downwardly on the holder and protective guard 38 to maintain sealing contact with the tube 34. The first protective cap 90 may then be removed to expose the longer end 84 of the needle 80, which may be inserted into a patient to extract a sample of blood. In this manner, the blood sampling tubes 34, blood sampling syringe assembly 36, and holder and protective guard 38 may be utilized to take one or more blood samples without requiring direct contact with the sampling needle 80 and while maintaining as sterile a sample as is possible under normal conditions. The blood sampling tubes 34, blood sampling syringe assembly 36 and holder and protective guard 38 may then be disassembled by reversing this process, with the thin membranes 74 of the blood sampling tubes 34 automatically closing over the puncture created by the short end 84 of the needle 80 to form a new sealing closure thereon.

Referring to FIGS. 1, 2, and 6, it may be seen that the wrapped inner specimen container 28 and lid 30, pair of blood sampling tubes 34, and blood sampling syringe assembly 36 are initially received within a generally cylindrical foam protective collar 108. The protective collar 108 is preferably formed from a closed cell polyethylene foams having a density of approximately 2.2 pounds per cubic foot (PCF) or approximately 0.035 gm/cm3. The protective collar 108 has a top surface 110 and a bottom surface 112 and a height measured therebetween which is approximately 4 cm. for a 10 cm. length tube 34 and 13 cm. height outer container 12. The protective collar 108 has approximately an 8 cm. diameter and defines a first or large diameter bore 114 which is radially offset by approximately one centimeter and which is sized to snugly and engagingly receive the specimen vial 28 therein. The protective collar also defines a pair of second or smaller diameter bores 116 which snugly and engagingly receive each of the sample tubes 34, and a third or syringe assembly bore 118 sized and shaped to snugly and engagingly receive the syringe assembly 36. The side wall 120 of the protective collar 108 adjacent to the larger bore 114 is cut to form a pair of opposing edges 122, 124 which define a gap of approximately one half to one centimeter therebetween when the collar 108 is unflexed The bores preferably extend completely through the protective collar 108 generally parallel to the body 24 of the outer container 12 and perpendicular to the top surface 110 of the protective collar 108 and the bottom portion 126 of the outer container 12.

The protective collar 108 is snugly received in the outer container 12 and is displaced from the bottom wall 126 thereof by a first or lower cushioning pad 128 constructed from a disk of 2 cm. thick open cell urethane polyester foam having approximately a 2.0 PCF or density of 0.032 gm/cm3. The specimen vial 28, sample tubes 34, and syringe assembly 36 are received in the bores 114, 116, 118 of the protective collar 108, with the holder and protective guard 38 being placed on top of the syringe assembly 36 as shown in FIG. 2. A second or upper cushioning pad 130 may be placed between the top of the sample tubes 34 and the interior of the lid 14 and held in place thereat by the sample tubes 34, specimen vial 28, and holder 38. Both the upper and lower cushioning pads 128, 130 therefore have a generally flexible but resilient shock absorbing property, and are more flexible but less resilient than the protective collar 108 which has greater shock absorbing properties than the upper and lower cushioning pads 128, 130.

An instruction manual 134 and a plurality of sealing tapes 136 may be placed surrounding the tubes 34 and specimen vial 28 against the inside surface 138 of the outer container body 12. A microbicidal sterilizing swab 140 such as a prepackaged towlette containing a 10% iodine solution is placed on top of the second or upper cushioning pad 130, and a desiccant material (not shown) may be included as appropriate. The instruction manual 134 may be in leaflet or booklet form, with instructions for obtaining and preserving the evidence sample, handling the apparatus 10 for transportation, and recording the chain of custody printed thereon. The instruction manual 134 should also contain a document upon which each intervening step in the collection and testing procedure may be recorded by the person undertaking that step of the procedure, so as to evidence and verify the chain of custody of the specimen vial 28 and blood sampling tubes 34.

The pair of sealing tapes 136 each have an adhesive backing and are affixed to a non-adhering backing strip 142 from which they may be removed by peeling the length of the tapes 136 away from and along the lengths of the strips 142. One tape 136 has a shorter length and narrower width sufficient to extend diagonally across the lid 30 of the specimen vial 28 and downwardly on both sides of the specimen vial 28 across the sealing collar 50, and a substantial distance downward along the outer surface 52 of the specimen vial 28. One tape 136 has a greater width and a greater length sufficient to extend diagonally across the lid 14 of the outer container 12 and downwardly on both sides of the container 12 across the sealing collar 22, and a substantial distance downward along the outer surface 24 of the container 12. Each sealing tape 136 is preferably constructed from a 32# paper with an adhesive coating which will not permit the tapes 136 to be removed without visibly tearing or delaminating, and each tape 136 should similarly have a printed safety pattern. The sealing tapes 136 should extend along the opposing sides of the respective vial 28 or outer container 12 a substantial distance such that said sealing tapes 136 cannot be removed without evidencing that removal.

In operation, the person initially obtaining the samples will break the seal on and unwrap the apparatus 10 from the tamper resistant outer wrapper which surrounds the outer container 12 and lid 14. The lid 14 is detached from the outer container 12, and the antiseptic swab 140, upper cushioning pad 130, and either the sealed specimen vial 28 and lid 30 or blood sample tubes 34 are removed from the outer container 12. Similarly, the instruction manual 134 and sealing tapes 136 are removed from the outer container 12.

Following the instructions provided on the instruction manual 134, the person removes the lid 30 and specimen vial 28 from the protective tamper-resistant wrapper 32. The biological fluid specimen is then placed directly into the specimen vial 28 up to a level between the indicators 56 showing a sufficient but not excessive quantity of fluid. The lid 30 is then inverted and engaged on the rim 42 of the specimen vial 28, being rotated corresponding to the direction of the threads 40, 42 in order to bring the adhesive surface 62 of the foam disk 60 into contact with the rim 42 so as to sealingly engage therewith around the periphery of the rim 42. The lid 30 should therefore be securely fastened to the specimen vial 28 such that the lower edge 48 of the skirt 46 closely confronts or engages the collar 50.

The shorter sealing tape 136 is then peeled from the corresponding backing strip 142 and applied to the lid 30 and side surfaces 52 of the specimen vial 28. The sealing tape 34 is firmly pressed into sealing contact with the lid 30 and vial 28 along the entire length of the sealing tape 136, as shown in FIG. 8.

Any necessary information concerning the individual supplying or the person collecting the fluid sample is then recorded on the specimen label 54, and the specimen vial 28 and lid 30 are slidingly inserted into the large bore 114 of the protective collar 108 in the outer container 12. The intervening steps are recorded on the document contained in the instruction manual 134 for verifying the chain of custody.

Similarly, a sample of blood may be taken using the blood sampling tubes 34, blood sampling syringe assembly 36, and holder and protective guard 38 as described in detail above. The blood sampling tubes 34 and blood sampling syringe assembly 36 may then be returned to the respective bores 116, 118 in the protective collar 108, and the holder 38 placed over the syringe assembly 36. The blood sampling tubes 34 may optionally be sealed using tapes (not shown) which cover the entire surface of the thin membrane 74 such that a needle may not be inserted through the stopper 72 without puncturing the sealing tape. Each blood sampling tube 34 should be marked with any necessary information prior to being placed in the protective collar 108, and the intervening steps are similarly recorded on the document contained in the instruction manual 134 for verifying the chain of custody, and this document is then placed in the outer container 12.

The upper cushioning pad 130 is then inserted into the outer container 12 above the top of the lid 30 of the specimen vial 28 and above the tops of the blood sampling tubes 34 and the holder 38, with the lid 14 of the outer container 12 then being engaged on the rim 18 of the outer container 12 and rotated thereon corresponding to the direction of the threads 16 in order to bring the lower edge 20 of the lid 14 into close confronting contact with the collar 22 of the outer container 12 to form a sealing contact therebetween.

The longer of the sealing tapes 136 is then peeled away from the corresponding backing strip 142 and applied to the lid 14 and outer container 12 in a manner similarly described above in relation to sealing the specimen vial 28 and lid 30. Any additional pertinent information may be recorded on the mailing or routing label 26, and the apparatus 10 may then be delivered to the appropriate laboratory or analytical testing facility.

For analysis, the technician removes the outer seal 136 from the outer container 12, removes the lid 12, upper cushioning pad 130, and visually inspects to make sure the contents are complete and intact. The blood sample tubes 34 and specimen vial 28 may then be removed and placed in a rack or holder (not shown) for use during the analysis.

Referring to FIG. 7, it may be seen that a technician or other laboratory personnel who will perform the necessary testing or analysis on the fluid evidence breaks the sealing tape 136 on the specimen vial 28 and lid 30, and completely unscrews the lid 30 from the specimen vial 28. The technician then removes all or a portion of the foam sealing disk 60 from the rim 42 of the specimen vial 28 by peeling it therefrom, or punctures the disk 60 with an appropriate instrument. The technician then removes aliquots of the fluid sample using a pipette 144 or other suitable instrument. The technician may then perform the necessary analysis on the aliquots of fluid removed from the specimen vial 28.

Similarly, the technician may remove any sealing tapes or anti-tampering indicia from the blood sample tubes 34, and remove the appropriate samples of blood from one or both of the tubes 34 using a syringe, pipette, or automated sampling machine. Each of these steps is recorded on the document contained in the instruction manual 134 for verifying the chain of custody, along with any additional pertinent information, and in some instances the test results may also be recorded on the same document.

While the preferred embodiment of the above apparatus 10 has been described in detail above with reference to he attached drawing figures, it is understood that various changes and adaptations may be made in the apparatus 10 without departing from the spirit and scope of the appended claims.

What is claimed is:

1. An apparatus for collecting and transporting a first sample and a second sample of biological materials for evidentiary purposes, said apparatus comprising:
   an outer container defining a receptacle region, said outer container having a bottom portion and a lid member mountable on said outer container opposing the bottom portion thereof;
   a specimen vial for removably receiving and containing a first sample;
   at least one sample tube for removably receiving and containing a second sample;
   a protective collar, said protective collar being received within the receptacle region of the outer container, said protective collar further defining a first bore extending at least partially through said protective collar and being sized to snugly and engagingly receive said specimen vial and at least one second bore extending at least partially through said protective collar and being sized to snugly and engagingly receive said sample tube;
   lower cushioning means disposed between said bottom portion of said outer container and both said specimen vial and said sample tube; and
   upper cushioning means disposed between said lid member of said outer container and both said specimen vial and said sample tube.

2. The apparatus of claim 1 wherein the sample tube is a blood sampling tube and the apparatus further comprises:
   a multi-sample syringe assembly, said syringe assembly including a retaining collar and a syringe needle which may be inserted into an interior region of the sample tube such that an end portion of said syringe needle is exposed, said syringe needle having a bore extending therethrough, said bore being in fluid communication with said interior region of the sample tube such that a fluid may pass through said bore into the interior region of the sample tube when the syringe needle is inserted into the sample tube, and a removable cover for enclosing said syringe needle, the protective collar defining a third bore extending at least partially through the protective collar and sized to snugly and engagingly receive said syringe assembly.

3. The apparatus of claim 2 wherein the syringe needle has an end portion, the apparatus further comprising:
   a protective guard, said protective guard having an interior region which may receive at least a portion of the sample tube, said protective guard further including means for engagingly receiving the syringe needle such that said syringe needle is inserted into the interior region of the sample tube when the sample tube is received within the interior region of the protective guard, the end portion of the syringe needle being exposed when the sample tube is received within the interior region of the protective guard, said protective guard being removably received within the outer container when the sample tube and syringe assembly are received in the second and third bores, respectively.

4. The apparatus of claim 1 wherein the number of sample tubes is two and the number of second bores is two.

5. The apparatus of claim 1 wherein the sample tube comprises:
   a glass test tube having a generally cylindrical body defining an open top; and
   a stopper mountable on said test tube to close the open top thereof, said stopper having a thin membrane portion aligned with said open top of said test tube.

6. The apparatus of claim 1 wherein the outer container and lid are enclosed in a tamper evident wrapper, with the specimen vial and sample tube received within the protective collar and the protective collar and first and second cushioning means received within the receptacle region of the outer container body.

7. The apparatus of claim 1 wherein the specimen vial comprises:
   a vial body, said vial body defining an open top and a receptacle region for containing the first sample;
   a vial lid, said vial lid being engagingly mountable on said vial body to form a removable closure over said open top;
   sealing means for selectively producing a removable fluid tight seal between said vial body and said vial lid;
   a tamper evident wrapper means, said wrapper means encasing said vial body, said vial lid, and said sealing means with said vial lid being inverted upon said vial body such that said sealing means does not form said fluid tight seal between said vial body and said vial lid until said vial lid is engagingly mounted on said vial body to form said removable closure.

8. The apparatus of claim 7 wherein the vial body has a peripheral rim adjacent to and surrounding the open top thereof, said sealing means comprising:
   a disk, said disk being received within the vial lid, said disk having a peripheral edge substantially conforming to the peripheral rim of the vial body, said disk having a surface coated with an adhesive, said adhesive extending across said surface of said disk at least around a portion of said disk adjacent to said peripheral edge of said disk, whereby said adhesive forms a fluid tight seal between said disk and the rim of the vial body when the surface of the disk coated with the adhesive is pressed into contact with the rim of the vial body when the vial lid is mounted on the vial body.

9. The apparatus of claim 8 wherein the rim is generally circular and the disk is generally circular, the disk and the rim each have a diameter, said diameter of the disk being slightly greater than or substantially equal to said diameter of the rim.

10. The apparatus of claim 1 wherein protective collar is formed from a closed cell foam material.

11. The apparatus of claim 10 wherein the closed cell foam material is polyethylene.

12. The apparatus of claim 1 Wherein the upper and lower cushioning means are formed from an open cell foam material.

13. The apparatus of claim 12 wherein the open cell foam material is a urethane polyester.

14. The apparatus of claim 1 wherein the outer container is generally cylindrical and the receptacle region of the outer container has a cross sectional diameter, the upper and lower cushioning means comprise:

a pair of disks, said disks each having a diameter substantially equal to the diameter of the receptacle region of the outer container, said disks being constructed of a first shock absorbing material.

15. The apparatus of claim 14 wherein the protective collar is formed from a second shock absorbing material, said second shock absorbing material from which the protective collar is formed having a greater density than the first shock absorbing material from which the pair of disks are formed.

* * * * *